US006184241B1

(12) United States Patent
Baures

(10) Patent No.: US 6,184,241 B1
(45) Date of Patent: Feb. 6, 2001

(54) ASPARTIC PROTEASE INHIBITORS

(75) Inventor: Paul W. Baures, Manhattan, KS (US)

(73) Assignee: Kansas State University Research Foundation, Manhattan, KS (US)

( * ) Notice: Under 35 U.S.C. 154(b), the term of this patent shall be extended for 0 days.

(21) Appl. No.: 09/139,221

(22) Filed: Aug. 24, 1998

(51) Int. Cl.[7] .................. A61K 31/415; A61K 31/41; C07D 233/22; C07D 231/10; C07D 249/04
(52) U.S. Cl. .................. 514/400; 514/406; 514/359; 548/333.5; 548/374.1; 548/255
(58) Field of Search .............. 548/333.5, 374.1, 548/255; 514/400, 406, 359

(56) References Cited

U.S. PATENT DOCUMENTS

| 5,326,780 | 7/1994 | Sugimoto et al. | 514/398 |
|---|---|---|---|
| 5,472,965 | 12/1995 | Sugimoto et al. | 514/252 |
| 5,597,926 | 1/1997 | Kempf et al. | 548/204 |
| 5,972,926 | * 10/1999 | Sandosham et al. | 514/185 |
| 5,998,424 | * 12/1999 | Galemo, Jr. et al. | 514/269 |

FOREIGN PATENT DOCUMENTS

96/05180     2/1996  (WO).

OTHER PUBLICATIONS

Hoog, et al "Human immunodeficiency virus protease ligand specificity conferred by residues outside of the active site cavity" Biochem 35:10279–86; 1996.

"Building blocks for HIV protease inhibitors" Aldrichimica Acta 31:1:16; 1998.

Han et al "Cyclic HIV protease inhibitors: Design and synthesis of orally bioavailable, pyrazole P2/P2 cyclic ureas with improved potency" J Med Chem 41:12:2019–2028; 1998.

Wlodawer et al "Structure–based inhibitors of HIV–1 protease" Annu Rev Biochem 62:543–85; 1993.

Clare "HIV protease: Structure–based design" Perspectives in Drug Discovery and Design 1:49–68; 1993.

Huff "HIV protease: A novel chemotherapeutic target for AIDS" Medicinal Chemistry 34:8:2305–2314; 1991.

Abdel–Meguid et al "An orally bioavailable HIV–1 protease inhibitor containing an imidazole–derived peptide bond replacement: Crystallographic and pharmacokinetic analysis" Biochemistry 33:39:11671–77; 1994.

Kempf et al "HIV protease inhibitors" Current Pharmaceutical Design 2:2:225–246; 1996.

Hubbard "Can drugs be designed? "Current Opinion in Biotechnology 8:696–700; 1997.

* cited by examiner

*Primary Examiner*—Deborah C. Lambkin
(74) *Attorney, Agent, or Firm*—Kurt D. Van Tassel; Deborah G. Vandenhoff; Van Tassel & Associates

(57) ABSTRACT

The present invention is directed to aspartic protease inhibitors, in particular to HIV protease, renin, pepsin and cathepsin D inhibitors. Inhibitors of the present invention have a 3 to 12-membered heterocyclic core containing at least two heteroatoms which interact with the carboxyl groups of the aspartic acid residues in the active site of the protease to inhibit the action thereof.

38 Claims, 3 Drawing Sheets

ASPARTIC PROTEASE INHIBITORS

FIELD OF THE INVENTION

The present invention relates to aspartic protease inhibitors, in particular to HIV protease, renin, pepsin and cathepsin D inhibitors.

BACKGROUND OF THE INVENTION

The inhibitors described below can be used for a number of aspartic proteases, such as HIV protease, renin, pepsin and cathepsin D. However, for ease of discussion, reference will be made to applying the described inhibitors to HIV protease. It will be well understood that optimization of inhibitors for renin, pepsin and cathepsin D may be required. The nature and scope of inhibitor modifications for such optimization will be readily apparent in view of the discussion below.

The human immunodeficiency virus (HIV) encodes an aspartic protease whose function is essential for proper virion assembly and maturation. Inactivation of HIV protease either by mutation or chemical inhibition leads to the production of immature, non-infectious viral particles. Accordingly, in attempts to find a drug for the treatment of AIDS, efforts have been directed to inhibitors of HIV protease.

HIV protease is unique in the family of aspartic proteases in that it is a homodimer which displays $C_2$ symmetry about the active site. The dimer is made up of two identical sub-units each contributing an aspartate residue to form a single active site. Known inhibitors are designed to inactivate HIV protease by interaction with the carboxylic acid functional group of one or both of the aspartic acid residues in the active site.

In the absence of a substrate, a water molecule bridges the two carboxyl groups of the aspartic acid residues by hydrogen bonding to two oxygen atoms; one from each of the carboxyl groups. In the active form of the enzyme, the two carboxyl groups thus interact closely and share one proton between them. Because of this interaction, one of the carboxyl groups has a lower $pK_a$ value, typically about 1.5, while the other carboxyl group has a higher $pK_a$, value, typically about 4.7.

Reduced amide inhibitors were among the earliest HIV protease inhibitors.

One of the more notable of these inhibitors is known as MVT-101. While the inhibitor does show activity against HIV protease, it is believed that the lack of functionality with the reduced amide (—$CH_2$—NH—) for hydrogen bonding to the aspartic acid residues is responsible for the moderate potency of the reduced amide inhibitors (Kempf, D. J. et al. *Current Pharmaceutical Design* 2:2:225–246; 1996).

Accordingly, most of the conventional inhibitors developed to date are the "so-called" transition-state analogs. Examples of transition-state analogs include statine-, hydroxyethylene- and hydroxyethylamine-containing inhibitors. These transition-state analog inhibitors share the common feature of a central hydroxyl group for hydrogen bonding to the carboxyl groups of the two aspartic acid residues in the active site.

The accepted mechanism of action for transition-state analog inhibitors is that the central hydroxyl group of the inhibitor replaces the water molecule that was bound in the active site of the enzyme in the absence of a substrate or inhibitor. The hydroxyl group acts as both a transition-state inhibitor and as a hydrogen bond donor-acceptor.

A common feature of hydroxyethylamine inhibitors is the presence of amine groups separated from the central hydroxyl group by 2 carbon atoms. No apparent interaction has been observed between the aspartic acid residues and the amine groups in the inhibitors (Huff, J. R. *Medicinal Chemistry* 34:8:2305–2314;1991).

In addition to the principal interaction between the central hydroxyl group and one or both of the carboxyl groups of the aspartic acid residues, there are a number of hydrogen bonds formed between the side chains of the inhibitor and sub-sites of the enzyme. The sub-sites of most interest in inhibitor design are termed the $S_1$, $S_1'$, $S_2$ and $S_2'$ sub-sites. Hydrogen bonding and other interactions between the atoms of the side chains and sub-sites helps stabilize the inhibitor in the active site of HIV protease (Wlodawer et al. *Annu Rev Biochem* 62:543–85; 1993).

Also, HIV protease has a pair of β-hairpin flaps that cover the active site. These flaps interact with the substrate or inhibitor to tightly bind a water molecule. This interaction is illustrated in Huff, J. R. (ibid) as being hydrogen bonds formed by the flap $Ile^{50}$ and $Ile^{50'}$ amide hydrogen atoms and the inhibitor carbonyl oxygen atoms on either side of a central hydroxyl group which hydrogen bonds to the aspartic acid residues. Thus, the water molecule bridges the inhibitor and the flaps. In the contracted conformation, the flaps form a pocketed hydrophobic tube shielding about 80% of the bound inhibitor from surrounding solvent (Huff, J. R., ibid).

One of the disadvantages of some of the known inhibitors is the poor pharmacokinetic properties and bioavailability of peptide analog inhibitors. High lipophilicity, high molecular weights, and the presence of numerous amide bonds contribute to less desirable pharmacokinetic properties and metabolic instability. Some researchers have therefore designed inhibitors in which an amide bond of a known tripeptide analog inhibitor has been replaced by an imidazole substituent, resulting in a substantial improvement of the pharmacokinetic properties and oral bioavailability of the inhibitor (Abdel-Meguid, S. S. et al. *Biochemistry* 33:39:11671–7; 1994).

Abdel-Meguid et al. disclose a hydroxyethylene tripeptide analog inhibitor in which the C-terminal carboxamide is replaced with imidazole to produce (2R,4S,5S,1'S)-2-phenylmethyl-4-hydroxyl-5-(tert-butoxycarbonyl)amino-6-phenylhexanoyl-N-(1'-imidazo-2-yl)-2'-methylpropanamide. The central hydroxyl group interacts with the carboxyl groups of the active site aspartic acid residues. The imidazole replaced the carbonyl oxygen and nitrogen atoms of the C-terminal carboxamide that formed hydrogen bonds with the $Asp^{29}$ α-amino group and the $Gly^{48}$ carbonyl group of the HIV protease. The imidazole ring provides improved solubility, which may allow more efficient uptake of the inhibitor into the intestinal mucosa. It is also believed that the imidazole substitution favorably influences metabolic stability and clearance.

Disadvantages of inhibitors known to date include poor solubility, metabolic stability and bioavailability. Also, synthesis of these inhibitors is complicated due to the number of asymmetric centers in each compound.

Accordingly, there is a need for aspartic protease inhibitors that have the potential for improved in vivo performance, and which are comparatively more economical and easier to synthesize.

SUMMARY OF THE INVENTION

According to one aspect of the present invention, there is provided an aspartic protease inhibitor having the following general formula (I):

$$Z—Het—Z \quad (I)$$

wherein,
a) Het is a saturated, partially unsaturated or unsaturated and substituted or unsubstituted 3 to 12-membered heterocyclic ring having
  i) at least two heteroatoms, wherein the first heteroatom can interact with a first aspartate residue in the active site of an aspartic protease and the second heteroatom can interact with a second aspartate residue in the same active site, and
  ii) a $pK_a$ value in the range from about 2.5 to about 12, and
b) wherein each Z can be the same or different, and has
  i) a shape complementarity with at least a portion of the substrate binding site of the protease;
  ii) a chemical structure for contacting multiple atoms of the substrate binding site; and
  iii) at least one R group, which can be the same or different, at least one R group having a chemical structure for occupying at least one sub-site, proximate to the active site of the aspartic protease.

According to another aspect of the present invention, there is provided an aspartic protease inhibitor having the following general formula (II):

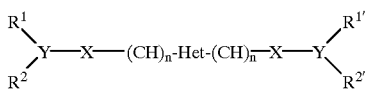

(II)

wherein,
a) Het is a saturated, partially unsaturated or unsaturated and substituted or unsubstituted 3 to 12-membered heterocyclic ring having
  i) at least two heteroatoms, wherein the first heteroatom can interact with a first aspartate residue in the active site of an aspartic protease and the second heteroatom can interact with a second aspartate residue in the same active site, and
  ii) a $pK_a$ value in the range from about 2.5 to about 12, and
b) X is a hydrogen bond-accepting group;
c) Y is a moiety having a backbone chain of at least 2 atoms selected from the group consisting of carbon, nitrogen, phosphorus, sulfur, oxygen, silicon and combinations thereof,
d) each $R^1$, $R^{1'}$, $R^2$ and $R^{2'}$ group is covalently bonded to the Y moiety, and at least one of $R^1$, $R^{1'}$, $R^2$ and $R^{2'}$ has a chemical structure for occupying at least one of the $S_1$, $S_1'$, $S_2$ and $S_2'$ sub-sites; and
e) n=0, 1, 2 or 3.

According to a further aspect of the present invention, there is provided an aspartic protease inhibitor having the following general formula (III):

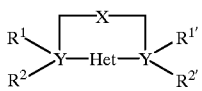

(III)

wherein,
a) Het is a saturated, partially unsaturated or unsaturated and substituted or unsubstituted 3 to 12-membered heterocyclic ring having
  i) at least two heteroatoms, wherein the first heteroatom can interact with a first aspartate residue in the active site of an aspartic protease and the second heteroatom can interact with a second aspartate residue in the same active site, and
  ii) a $pK_a$ value in the range from about 2.5 to about 12, and
b) X is a hydrogen bond-accepting group;
c) Y is a moiety having a backbone chain of at least 2 atoms selected from the group consisting of carbon, nitrogen, phosphorus, sulfur, oxygen, silicon and combinations thereof; and
d) each $R^1$, $R^{1'}$, $R^2$ and $R^{2'}$ group is covalently bonded to the Y moiety, and at least one of $R^1$, $R^{1'}$, $R^2$ and $R^{2'}$ $R_2'$ has a chemical structure for occupying at least one of the $S_1$, $S_1'$, $S_2$ and $S_2'$ sub-sites.

BRIEF DESCRIPTION OF THE DRAWINGS

In drawings which illustrate bioactivity of a selection of inhibitors according to the present invention.

DETAILED DESCRIPTION OF THE INVENTION

Figure 1:
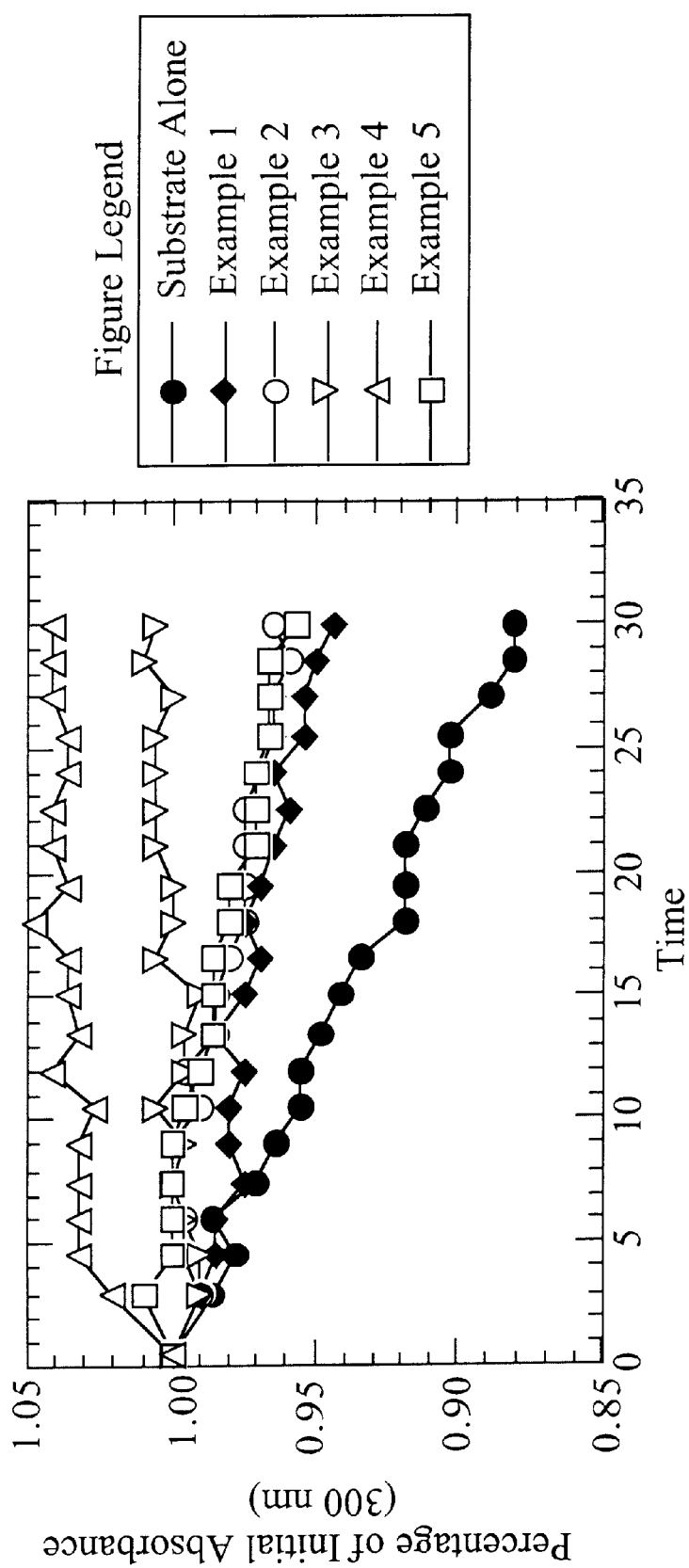
FIG. 1 is a graphical representation of the bioactivity of deprotected compounds prepared in Examples 1–5 at $10 \mu M$ in DMSO.

The HIV protease inhibitors of the present invention interact with the catalytic aspartic acid residues in the active site of HIV protease to inhibit the action thereof. The HIV protease inhibitors of the present invention have a 3 to 12-membered heterocyclic ring containing at least two heteroatoms which interact with the carboxyl groups of the aspartic acid residues. This is in contrast to the majority of known inhibitors where the functional group for bonding to the carboxyl groups of the aspartic acid residues of HIV protease is a hydroxyl group.

The compounds of the present invention are illustrated by the following general formula (I)

$$Z—Het—Z \quad (I)$$

wherein Het is a saturated, partially unsaturated or unsaturated and substituted or unsubstituted 3 to 12-membered heterocyclic ring having at least two heteroatoms and each Z can be the same or different, and has a shape complementarity with at least a portion of the substrate binding site of the protease; a chemical structure for contacting multiple atoms of the substrate binding site; and at least one R group, which can be the same or different, at least one R group having a chemical structure for occupying at least one sub-site, proximate to the active site of the aspartic protease.

The heterocycle provides (1) a heterocyclic conformational constraint with (2) a suitable $pK_a$ value (3) for interaction with the carboxyl functional groups of the active site aspartic acid residues. Each of these features is discussed in more detail below.

First, the heterocyclic core provides conformational constraint for presentation of the R groups to sub-sites in the active site of the enzyme. The conformational constraint may result in R groups that are defined by torsion angles of 0° to approximately 120° between one another.

The heterocyclic core may be saturated, partially unsaturated or unsaturated. Preferably, the heterocycle is a 3 to 10-membered ring. More preferably, the heterocycle is a 3 to 7-membered ring and most preferably, a 5 to 7-membered ring. Unsaturated and aromatic rings are inherently planar and will provide a higher degree of conformational constraint than will the saturated counterparts. Planar aromatic heterocycles are comparatively easily synthesized and commercially available. Preferably, the heterocyclic core is at least partially unsaturated proximate the heteroatoms.

While not as preferred, saturated heterocydes will also offer conformational constraint even though such heterocycles are not planar. Accordingly, saturated heterocycles can be used in the inhibitors of the present invention. The conformational analysis of small ring structures, i.e., 3 to 6 atoms, is well-known and predictable.

Second, the heterocyclic ring must be chosen to have a proper $pK_a$ value to allow for an amphoteric acid-base interaction with the two catalytic aspartic acid residues. Preferably, the $pK_a$ value is in the range of from about 2.5 to about 12. More preferably, the $pK_a$ value is in the range of from about 5 to about 7.

Third, the heterocyclic ring has hydrogen bond complementarity for concurrent association with the two carboxylic acid groups of the aspartic protease. The resulting protonation states of the two carboxylic acid groups and the heterocyclic ring stabilizes the enzyme-inhibitor complex.

The heterocycle has at least two heteroatoms which interact with the two carboxyl groups of the active site aspartic acid residues. Preferably, the heterocycle has 2 to 4 heteroatoms. More preferably, the heterocycle has 2 to 3 heteroatoms and most preferably, two heteroatoms. Suitable heteroatoms of the heterocycle include nitrogen, phosphorous, oxygen, sulfur, boron, silicon and combinations thereof. Preferably, at least one of the heteroatoms is nitrogen. More preferably, the heterocycle has two nitrogen atoms.

Examples of suitable heterocycles include, without limitation, imidazole, imidazolidine, pyrazole, triazole, oxazole, thiazole, pyridazine, pyrimidine, pyrazine, piperazine, triazine, oxazine and 1,4 diazobicyclo-2,2,2-octane.

In addition to the appended Z groups, the heterocyclic core may be substituted or unsubstituted. Examples of substituents include, without limitation, acyl, aldehyde, alkyl, amido, amino, aryl, carboxamide, carboxyl, ether, halo, hydroxyl, nitro, oxime, sulfonyl, and sulfoxide groups.

Without being bound by theory, it is believed that the interactions between the heterocyclic inhibitors of the present invention and the aspartic acid residues in the active site is that of (1) a general acid-general base, (2) a simple base or (3) a combination thereof. These types of interactions are illustrated below, without limitation, in Scheme 1 wherein the heterocycle is an imidazole ring.

Scheme 1

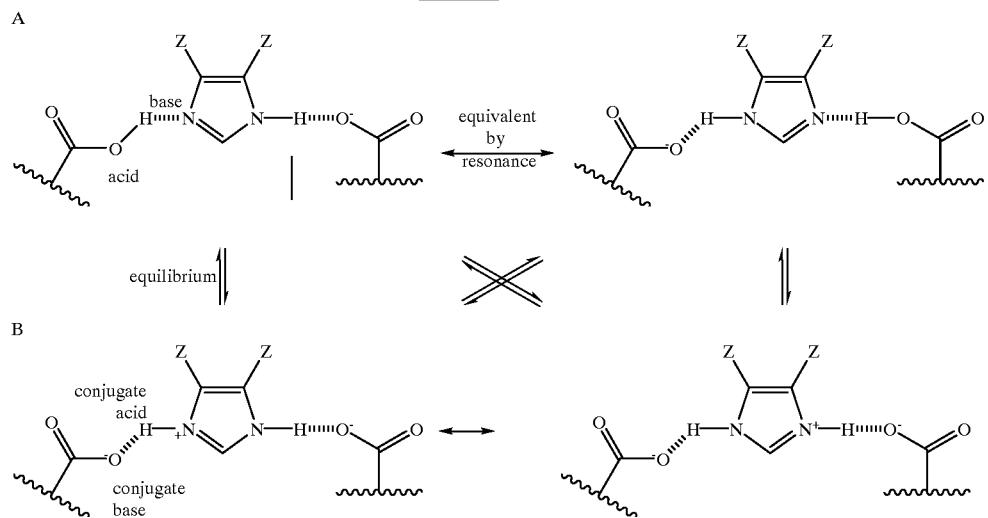

The two structures in interaction A of Scheme 1 are equivalent because it does not matter which carboxylic acid is shown as deprotonated. The transfer of a proton from the second aspartate to the imidazole can also yield two equivalent structures shown in interaction B of Scheme 1. These structures can all coexist and, on the basis of the reported $pK_a$ values of the catalytic aspartate residues ($pK_{a1}$ and $pK_{a2}$ are 1.5 and 4.7, respectively) and that of an imidazole ring $pK_a$=6.0–7.0), it is believed that about 10% of interaction A would be present along with about 90% of interaction B.

The nitrogen atoms of imidazole are separated by an intermediary carbon atom. Without being bound by theory, it is believed that the relatively acidic C—H group in the imidazole ring can provide further stabilization of the inhibitor/protease interaction. This additional interaction is depicted in Scheme 2 below.

Scheme 2

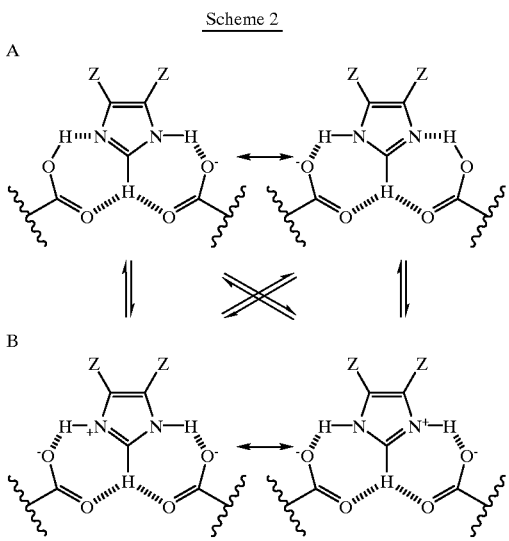

The interactions between the nitrogen atoms of the imidazole ring and the carboxyl groups of the active-site aspartic acid residues are believed to be the same as those depicted in Scheme 1.

The proton transfer shown in A and B of Scheme 1 allows for all of the interactions to co-exist in the inhibitors of the present invention. This is in contrast to known inhibitors discussed in the background section herein which do not provide for these types of interactions. Also, the additional stabilization provided by interaction with the hydrogen atom pendant to an intermediate carbon atom is not provided in the known inhibitors.

The proposed interaction between another inhibitor of the present invention, such inhibitor containing a pyrazole heterocycle, and the carboxyl groups of the active-site aspartic acid residues of HIV protease is illustrated in Scheme 3 below.

Scheme 3

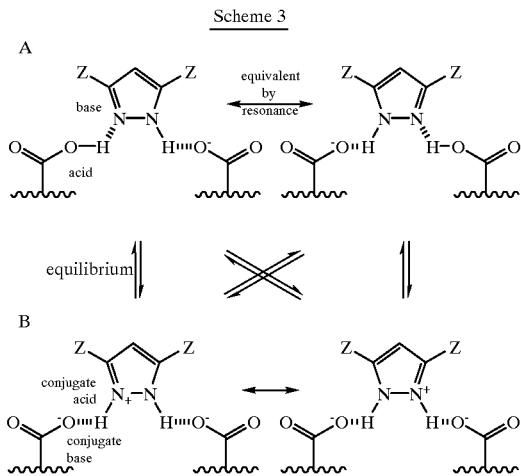

As depicted above, there is no intermediate C—H group between the two nitrogen atoms of the pyrazole group. Accordingly, there is no additional interaction between the heterocycle and the carboxyl groups of the aspartic acid residues. However, the pyrazole is much more acidic than the imidazole (i.e., $pK_a$=2.5 v. $pK_a$=6.0–7.0) and is also able to transfer a proton to the carboxyl group. Similar to Scheme 1, the two structures in interaction A of Scheme 3 are equivalent because it does not matter which carboxylic acid is shown as deprotonated. The transfer of a proton from the second aspartate to the pyrazole can also yield two equivalent structures shown in interaction B of Scheme 3. These structures can all coexist and, on the basis of the reported $pK_a$ values of the catalytic aspartate residues ($pK_{a1}$ and $pK_{a2}$ are 1.5 and 4.7, respectively) and that of an pyrazole ring ($pK_a$=2.5), it is believed that about 99% of interaction A would be present along with about 1% of interaction B.

The Z groups appended to the heterocyclic core of the inhibitors of the present invention are selected to complement the remaining features of the substrate-binding site, as will be discussed in more detail below.

Each Z group can be the same or different, and has (a) a shape complementarity with at least a portion of the substrate binding site of the protease, (b) a chemical structure for contacting multiple atoms of the substrate binding site, and (c) at least one R group, which can be the same or different, at least one R group having a chemical structure for occupying at least one sub-site, proximate to the active site of the aspartic protease.

Inhibitors of the present invention, having a heterocyclic core and Z groups selected according to the above criteria, will have 3 or more of the following properties: (1) improved binding constant (i.e., potency) of the inhibitor to the enzyme; (2) low plasma protein binding; (3) an overall chemical structure which allows for water solubility; (4) an overall chemical structure which allows for complete tissue distribution; (5) improved oral bioavailability; (6) metabolically stable chemical functional groups; (7) a molecular weight less than about 600 to reduce potential elimination problems; (8) improved resistance to mutant viruses; and (9) functional groups which avoid metabolic problems or potential drug interactions.

The Z group is selected to provide shape complementarity with at least a portion of the substrate binding site of the protease. Research efforts have led to X-ray crystal structures which characterize, on an atomic level, the structure of HIV protease. Accordingly, surfaces and cavities in the substrate binding site have been identified. It is therefore possible, using structure-based design (discussed in more detail below), to select and/or assess the shape of an inhibitor for its complementarity to the shape of the substrate binding site. The shape of the Z groups are selected to have a shape which is complementary to the enzyme substrate binding site.

The Z group is also selected to provide contacts between the inhibitor and the enzyme. Contacts are defined as chemical, physical and/or physicochemical interactions. Contacting distances are preferably interatomic distances of < about 4.1 Å for non-hydrogen atoms. The number of contacts of conventional inhibitors is presented in Wlodawer et al. (ibid) as ranging from 123 to 181. It is believed that the improved binding between the aspartate residues and the inhibitor of the present invention, as well as the conformational constraint provided by the heterocyclic core of the present invention will allow for smaller Z groups and therefore a reduced number of contacts will be required to stabilize the inhibitor/protease complex. For example, the number of contacts between atoms of the inhibitor and atoms of the substrate-binding site may be as low as about 50 contacts.

For example, preferably a Z group of an HIV protease inhibitor of the present invention has a functional group for binding to the amide groups of the flap Ile[50] and Ile[50'] residues, either directly or indirectly through a water molecule. The functional group is preferably a hydrogen bond-accepting group such as, for example, a carbonyl group, a sulfoxide group, a sulfone group, a phosphine oxide group, an amine oxide group or a hydroxylamine group.

Each Z group preferably has at least one substituent R group to occupy one or more of the $S_1$, $S_1'$, $S_2$ and $S_2'$ sub-sites. The $S_1/S_1'$ sub-sites are principally hydrophobic binding pockets. The $S_2/S_2'$ sub-sites have dual hydrophobic and hydrophilic (i.e., amphoteric) character. Some conventional HIV protease inhibitors have been prepared using hydrophobic residues with hydrogen bonding functional groups to improve overall properties. Preferably, Z is a moiety with one or more atoms selected from the group consisting of hydrogen, carbon, nitrogen, oxygen, sulfur, boron, silicon, phosphorus, fluorine, chlorine, bromine, iodine and combinations thereof.

The Z groups may be symmetrical or asymmetrical. HIV protease is a homodimer made up of two identical sub-units. The homodimer displays $C_2$ symmetry about the active site. Many of the conventional inhibitors are asymmetric, even though HIV protease is symmetric about the active site. Asymmetric inhibitors often bind in a manner to conserve sub-site symmetry in the complex and conventional symmetrical inhibitors do not always provide improved properties (Wlodawer et al., ibid). It is believed that the heterocyclic core of the inhibitors of the present invention will allow for symmetrical Z groups, because the rigid structural heterocyclic core is placed at the C2 axis within the enzyme active site, thereby forming an inhibitor with $C_2$ symmetry. An inhibitor with such symmetry is expected to have improved potency versus conventional symmetric inhibitors.

In one embodiment of the present invention, an HIV protease inhibitor of the present invention is represented by the following general formula (II):

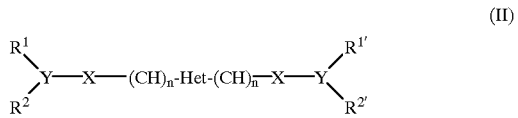

(II)

where Het is a saturated, partially unsaturated or unsaturated and substituted or unsubstituted 3 to 12-membered heterocyclic ring containing at least two heteroatoms; X is a hydrogen bond-accepting group; Y is a moiety having a backbone chain of at least 2 atoms sufficient to present at least one of $R^1$, $R^{1'}$, $R^2$ and $R^{2'}$ to the $S_1$, $S_1'$, $S_2$ and $S_2'$ sub-sites, respectively; at least one of $R^1$, $R^{1'}$, $R^2$ and $R^{2'}$ having a chemical structure to occupy the $S_1$, $S_1'$, $S_2$ and $S_2'$ sub-sites; and n is 0, 1, 2 or 3.

Examples of X are, without limitation, carbonyl, sulfoxide, sulfone, phosphine oxide, amine oxide or hydroxylamine groups.

Preferably, $R^1$ is a group selected to occupy the $S_1$ sub-site, $R^{1'}$ is a group selected to occupy the $S_1'$ sub-site and is the same as or different than $R^1$, $R^2$ is a group selected to occupy the $S_2$ sub-site, $R^{2'}$ is a group selected to occupy the $S_2'$ sub-site and is the same as or different than $R^2$.

Depending on the heterocyclic core used, the hydrogen bond-accepting group may be distanced from the heterocyclic core by a methylene group on one or both sides of the heterocyclic core to provide the distance and/or orientation required to interact with the flap $Ile^{50}$ and $Ile^{50'}$ residues.

Preferably, the atoms of the backbone chain are carbon, nitrogen, phosphorus, sulfur, oxygen, silicon and combinations thereof. Examples of Y are, without limitation, substituted or unsubstituted, branched or unbranched alkyl, alkylamine, alkoxy, alkoxyamine, thioalkyl, thioalkoxy, thioalkoxyamine, thioalkylamine, phosphidoalkyl, phosphidoalkoxy, phosphidoalkoxyamine and phosphidoalkylamine groups. Y may also include functional groups to provide additional interaction between the inhibitor and the substrate-binding site.

It is well understood by those skilled in the art that effective HIV protease inhibitors have R groups that interact similarly with the sub-sites of the enzyme. For example, Wlodawer et al. (ibid, at pp. 558–561) evaluated the structural similarities of 12 different HIV protease inhibitors, when bound in the protease active site in an extended conformation. They reported that the functional elements of each of the inhibitors were substantially aligned overall when the structures were superimposed with one another. This observation is evidence that the side chains (i.e., R groups) of each of the inhibitors interact similarly, and thereby conform with, the sub-sites in the HIV protease. Although one or two non-conforming R groups are unlikely to fully negate an inhibitor's performance, they could diminish an inhibitor's effectiveness. Therefore, most preferably, each of the R groups has the appropriate size, architecture and hydrophilic/hydrophobic character to conform with each of the sub-sites, while the Y moieties provide an appropriate extension for properly presenting the R groups to their respective sub-sites.

Examples of suitable $R^1$, $R^{1'}$, $R^2$ and $R^{2'}$ groups are, without limitation, substituted or unsubstituted, branched or unbranched, $C_1-C_6$ alkanes, $C_1-C_6$ alkenes and $C_1-C_6$ alkynes; substituted or unsubstituted, branched or unbranched $C_3-C_9$ cycloalkanes and $C_3-C_9$ cycloalkenes; and substituted or unsubstituted aromatic hydrocarbon and heterocyclic rings. Examples of suitable substituents are, without limitation, acyl, aldehyde, alkyl, amido, amino, aryl, carboxamide, carboxyl, ether, halo, hydroxyl, nitro, oxime, phosphido, sulfonyl and sulfoxide groups. $R^1$, $R^{1'}$, $R^2$ and $R^{2'}$ may be the same or different. $R^1$, $R^{1'}$, $R^2$ and $R^{2'}$ may also contain one or more amino acids. However, it is preferred that the $R^1$, $R^{1'}$, $R^2$ and $R^{2'}$ groups do not contain amino acids because of the associated bioavailability problems.

Preferably, $R^1$ and $R^{1'}$ are phenyl, benzyl, t-butyl, i-butyl, or i-propyl groups. Preferably, $R^2$ and $R^{2'}$ are a tetrahydrofuranyl ring, a substituted benzamide, a 2-amino-1-hydroxyindan ring, or a substituted pyrazole.

Without being bound by theory, it is believed that the interaction of an HIV protease inhibitor, of the general formula (II) of the present invention, with the aspartic acid residues of the active site, the $S_1$, $S_1'$, $S_2$ and $S_2'$ sub-sites, and the flap $Ile^{50}$ and $Ile^{50'}$ residues is as shown in Scheme 4, wherein the heterocycle is an imidazole ring, X is a carbonyl group, n is 0, Y is —NH—CH$_2$—COO—, $R^1$ and $R^{1'}$ are benzyl groups and $R^2$ and $R^{2'}$ are t-butyl groups.

Scheme 4

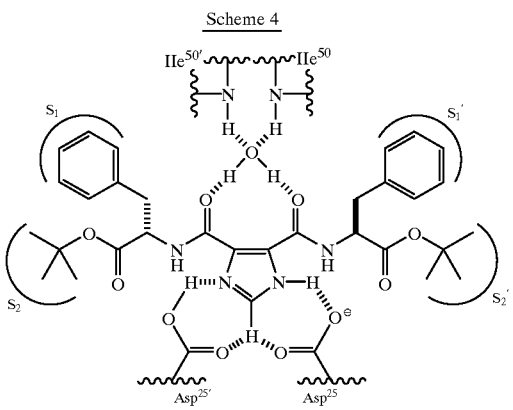

Scheme 4 illustrates interaction between the imidazole ring and the carboxyl groups of the aspartic acid residues, as described in Scheme 2. However, Scheme 4 does not illustrate any other contacts between the inhibitor and the substrate-binding site. The benzyl groups occupy the $S_1$ and $S_1'$ sub-sites and the t-butyl groups occupy the $S_2$ and $S_2'$ sub-sites. The flap $Ile^{50}$ and $Ile^{50'}$ residues are bound to the carbonyl groups adjacent the heterocyclic core through a water molecule.

In another embodiment of the present invention, an HIV protease inhibitor of the present invention is represented by the following general formula (III):

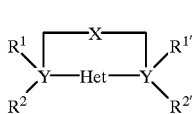

(III)

wherein Het, Y, X, $R^1$, $R^{1'}$, $R^2$ and $R^{2'}$ are defined as above in general formula II.

Selection of Z groups may be accomplished by applying structure-based drug design and/or analog-based drug design principles known to those skilled in the art.

The use of structure-based design in HIV protease inhibitor modeling is discussed in Clare, M. *Perspectives in Drug Discovery and Design* 1:49–68; 1993.

Structure-based drug design techniques include: X-ray crystallography, NMR spectroscopy, and molecular modeling. The most widely used technique is X-ray crystallography. This method provides a 3-dimensional representation of the interaction between the protease and a bound inhibitor. Detailed information regarding the bound conformation of the inhibitor and of the interactions between enzyme and inhibitor can be obtained from this technique. It is, therefore, possible to determine whether addition of another functional group is required, if it is desirable to enhance binding in the enzyme/inhibitor complex, or whether the modification of an existing R group would enhance the binding.

In this manner, the design, synthesis, and biological assessment of protease inhibitors can be used iteratively with X-ray crystallography results to optimize inhibitor interactions.

NMR spectroscopy has been used in an analogous manner although this technique can be more difficult to use and the results may be more difficult to interpret.

Molecular modeling can be employed in multiple ways to the process of R group optimization. The characteristics (shape, electronic, and hydrophobic character) of the active-site and surrounding sub-sites can be determined by various modeling methods. Then, comparison of a bound inhibitor with these "ideal" characteristics may identify beneficial changes to an inhibitor to improve complementarity between inhibitor and enzyme.

Examples of software used by companies and researchers involved in drug design are SYBYL (Tripos, St. Louis, Mo.), CERIUS 2 (Molecular Simulations Inc., San Diego, Calif.), DISCOVER (Molecular Simulations Inc., San Diego, Calif.), SPARTAN and DOCK (UCSF, CA).

In analog-based drug design, a 3-dimensional structure of the enzyme is not known empirically although a model of the enzyme may be proposed. For these cases, the biological activity of the inhibitors directs the discovery and optimization process. Quantitative structure-activity relationships (QSAR) can be determined for a variety of functional group changes to the original inhibitor(s). The methodology for converting information from QSAR studies to an optimized inhibitor has been extensively utilized in drug design. Modeling may also play an important role in analyzing the active inhibitors to find which characteristics (shape, electronic, and hydrophobic character) may be similar when bound to the enzyme. These studies are called 3D-QSAR techniques and application of this technique for HIV protease inhibitors is well known to those skilled in the art. Such techniques can be similarly employed to optimize the selection of R groups for inhibitors of the present invention.

Optimization of these interactions can then proceed beginning with election of a heterocyclic core and working away from the active site towards he sub-sites sequentially. Thus, the heterocycles can be first altered to determine the best choice for interacting with the active site aspartic acid residues. Concurrent with these design experiments will be a decision of whether a hydrogen bond-accepting group will be necessary to orient the conserved water for flap binding. Optimized binding is likely to require this interaction and so it is likely that a hydrogen bond-accepting group will be included in the final compound. In this case it is then necessary to consider both the distance and geometry of the hydrogen bond-accepting group while choosing the heterocyclic ring. For example, if two carbonyl groups are used to bind the flap $Ile^{50}$ and $Ile^{50'}$ residues to the inhibitor, each heterocycle will offer slightly different distances between the oxygen atoms of the carbonyl groups as well as a different torsion angle (measured by using the oxygen and carbon atoms of the two carbonyl groups) to define the relative orientation of the two carbonyl groups to each other.

In this manner it may be possible to make changes to the two Z groups off the heterocyclic core until an optimized compound is obtained and then simply remove one of the two Z groups to yield an monosubstituted heterocyclic inhibitor. This may compromise the overall properties of the inhibitor. However, the compound may still exhibit modest inhibitory potency and perhaps even improved pharmacokinetic properties due to the smaller size.

The protease inhibitors of the present invention are also suitable to inhibition of renin, pepsin and cathepsin D. However, since the substrate-binding sites of renin, pepsin and cathepsin 0 differ from that of HIV protease, Z group selection may require alteration in the functional groups and spacing thereof to provide a stabilized enzyme/inhibitor complex. For example, while HIV protease has a pair of β-hairpin flaps that cover the active site, pepsin has only one such flap.

The protease inhibitors of the present invention are useful for the treatment or prophylaxis of diseases and conditions caused or assisted by the action of aspartic proteases. In particular, the inhibitors of the present invention are useful for the treatment or prophylaxis of HIV. However, the protease inhibitors of the present invention are also useful for inhibiting cathepsin D which is a lysosomal enzyme that degrades proteins intracellularly, renin which catalyzes removal of the decapeptide angiotensin I which plays an major role in the control of blood pressure, and pepsin which is a gastric enzyme involved in digestion.

The following non-limiting examples of selected inhibitors are provided for illustrative purposes only.

EXAMPLE 1

Preparation of 4,5-Bis{[(1,1-dimethylethoxy)-(S)-phenylalanyl]carbonyl}-1H-imidazole

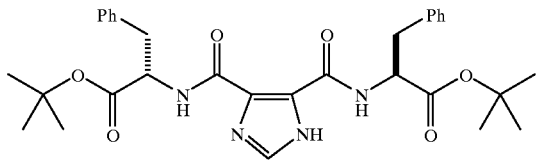

10 mL of anhydrous $CH_2Cl_2$ was added to a dry round-bottom flask, followed by the addition of imidazole-4,5-dicarboxylic acid (0.5 g, 3.20 mmol), 1-hydroxybenzotriazole monohydrate (0.87 g, 6.41 mmol), and L-phenylalanine t-butyl ester hydrochloride (2.06 g, 8.01 mmol) under a blanket of inert gas. This stirred suspension was cooled to 0° C. and triethylamine (1.12 mL, 8.01 mmol) was added dropwise. This helped solubilize some of the remaining solids but not all of them. Finally, dicyclohexylcarbodiimide (1.39 g, 6.72 mmol) was added to the mixture all at once. The suspended imidazole-4,5-dicarboxylic acid slowly dissolved and gave way to precipitated dicyclohexylurea. The reaction mixture was stirred for 24 hours and the precipitated solids were removed by filtration. The dichloromethane was diluted with 80 mL ethyl acetate before washing the solution with 20 mL each of 5% citric acid, 1 M $NaHCO_3$, $H_2O$ and a saturated NaCl solution. The organic fraction was dried over anhydrous $MgSO_4$, filtered, and concentrated to a white foam. Final purification was done on a silica gel column by gravity chromatography with ethyl acetate/hexane (50/50) as the eluent. The fractions containing the desired product were combined and concentrated to yield 455 mg pure material for a 25% yield.

EXAMPLE 2

Preparation of 3,5-Bis{[(1,1-dimethylethoxy)-(S)-phenylalanyl]carbonyl)-1H-pyrazole

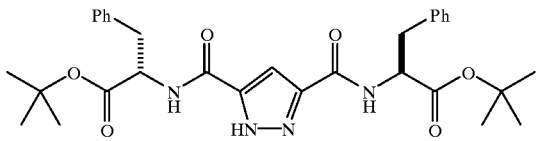

This compound was prepared in an analogous manner to the compound prepared in Example 1, using 1H-pyrazole-3,5-dicarboxylic acid instead of imidazole-4,5-dicarboxylic acid. The fractions containing the desired product were combined and concentrated with an 8% yield.

EXAMPLE 3

Preparation of 4,5-Bis{[(1,1-dimethylethoxy)-(S)-phenylalanl]carbonyl}-1H-1,2,3-triazole

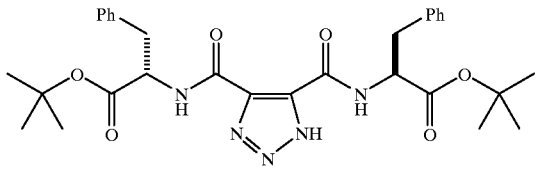

This compound was prepared in an analogous manner to the compound prepared in Example 1, using 1H-1,2,3-triazole-4,5-dicarboxylic acid instead of imidazole-4,5-dicarboxylic acid. The fractions containing the desired product were combined and concentrated with a 2% yield.

EXAMPLE 4

Preparation of 4,5-Bis{[(1,1-dimethylethoxy)-(S)-valyl]-(S)-phenylalanyl}carbonyl}1H-imidazole

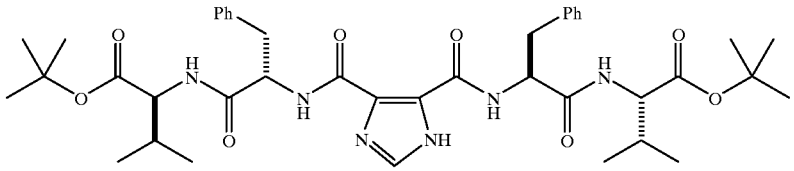

2 mL each of anhydrous dichloromethane and trifluoroacetic acid was added to a dry round-bottom flask containing 4,5-bis{[(1,1-dimethylethoxy)-(S)-phenylalanyl]carbonyl}-1H-imidazole. This solution was stirred for 4 hours. Shortly thereafter, using TLC analysis, it was determined that the starting material was entirely consumed. The dichloromethane and trifluoroacetic acid were removed under vacuum and the resulting solid was dissolved in dichloromethane before removing the solvent under vacuum. This step was repeated three times before coupling the material to L-valine t-butyl ester hydrochloride by the method outlined in Example 1.The fractions containing the desired product were combined and concentrated with a 14% yield.

EXAMPLE 5

Preparation of 3,5-Bis{{[(1,1-dimethylethoxy)-(S)-valyl]-(S)-phenylalanyl}carbonyl}1H-pyrazole

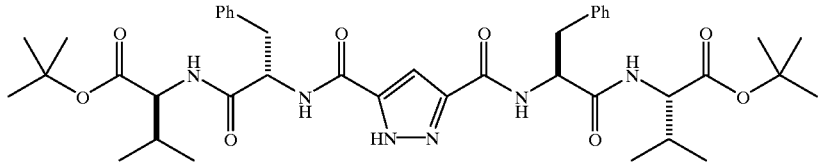

This compound was prepared in an analogous manner to the compound prepared in Example 4, using 3,5bis{[(1,1-dimethylethoxy)-(S)-phenylalanyl]carbonyl}-1H-pyrazole instead of 4,5-bis{[(1,1-dimethylethoxy)-(S)-phenylalanyl]carbonyl}-1H-imidazole. The fractions containing the desired product were combined and concentrated with a 16% yield.

EXAMPLE 6

Preparation of Bis[(1,1-dimethylethoxy)-(S)-phenylalanyl]-maleoyl (Control)

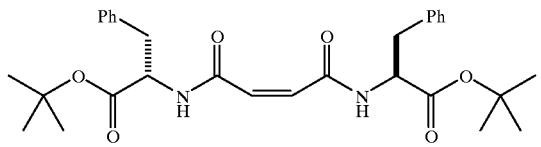

This compound was prepared in an analogous manner to the compound prepared in Example 1, using maleic acid instead of imidazole-4,5-dicarboxylic acid. The fractions containing the desired product were combined and concentrated with an 11% yield.

EXAMPLE 7

Bioassay of prepared compounds

The compounds prepared in Examples 1–5 were tested according to the method described in Richards, A. D. et al. (*FEBS Letters* 247:113–117; 1989) using a colorimetric peptide substrate which can be monitored for cleavage either in the absence or presence of an inhibitor. Acetylpepstatin was employed as a control inhibitor and bis[(1,1-dimethylethoxy)-(S)-phenylalanyl]-maleoyl, prepared in Example 6, was used as a control compound.

The compounds prepared in Examples 1–5 were deprotected with 4 N HCl in dioxane for 8 hours prior to solution formation at 10 μM in DMSO. The compounds obtained by deprotection were used without further purification.

The control reaction with substrate alone contained equivalent amounts of DMSO. These results are shown in FIG. 1. The data is reported as a change in the percent absorbance relative to the initial absorbance which itself is normalized to a value of 1. In data not shown, the protease was shown to still be active after 60 minutes by adding additional substrate.

Figure 2:
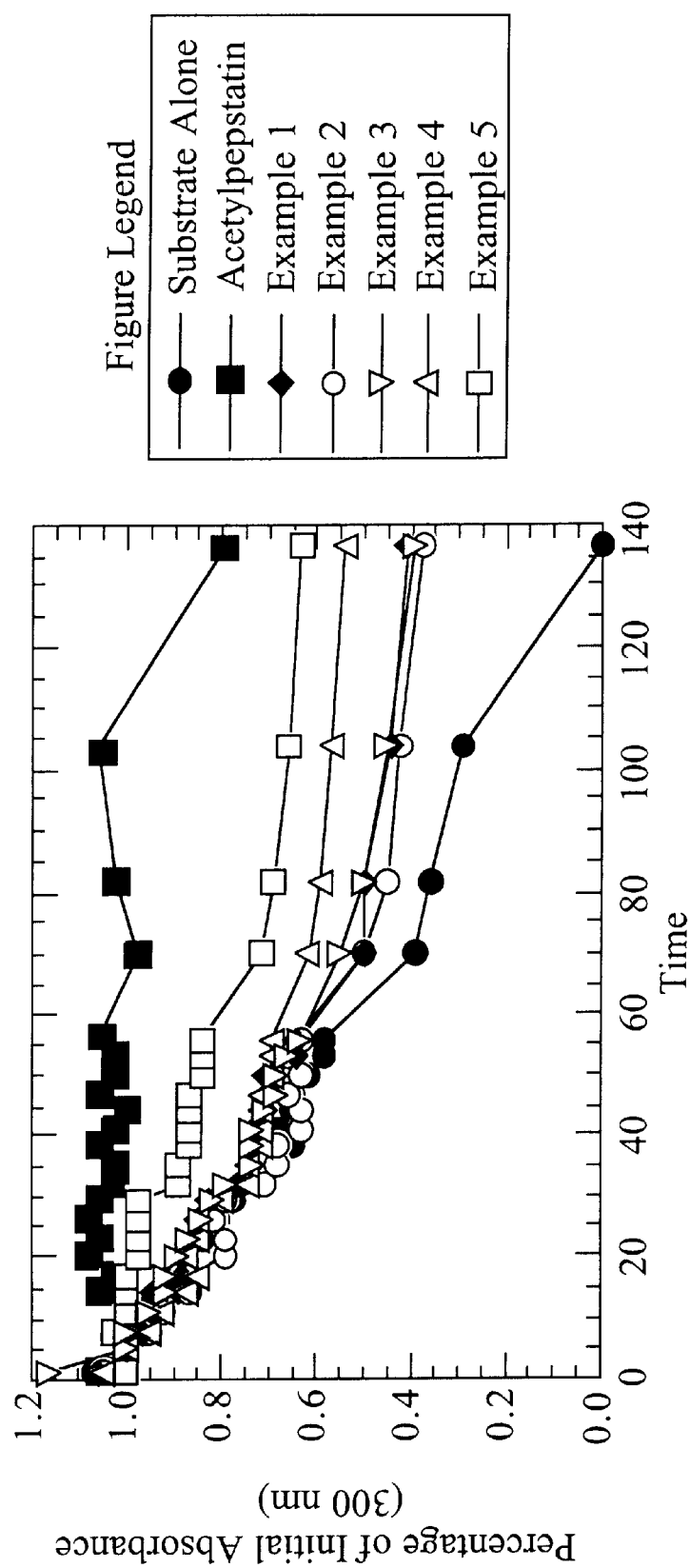
FIG. 2 is a graphical representation of the bioactivity of deprotected compounds prepared in Examples 1–5 at $1 \mu M$ in DMSO.

These compounds were also tested as 1 μM solutions in DMSO and compared against the standard inhibitor acetylpepstatin at 3.5 μM. The results of this experiment are shown in FIG. 2 after normalization of the initial absorbance and adjusting the final absorbance value of the substrate to represent 100% cleavage (no significant decrease in absorbance was observed after 137 minutes).

Figure 3:
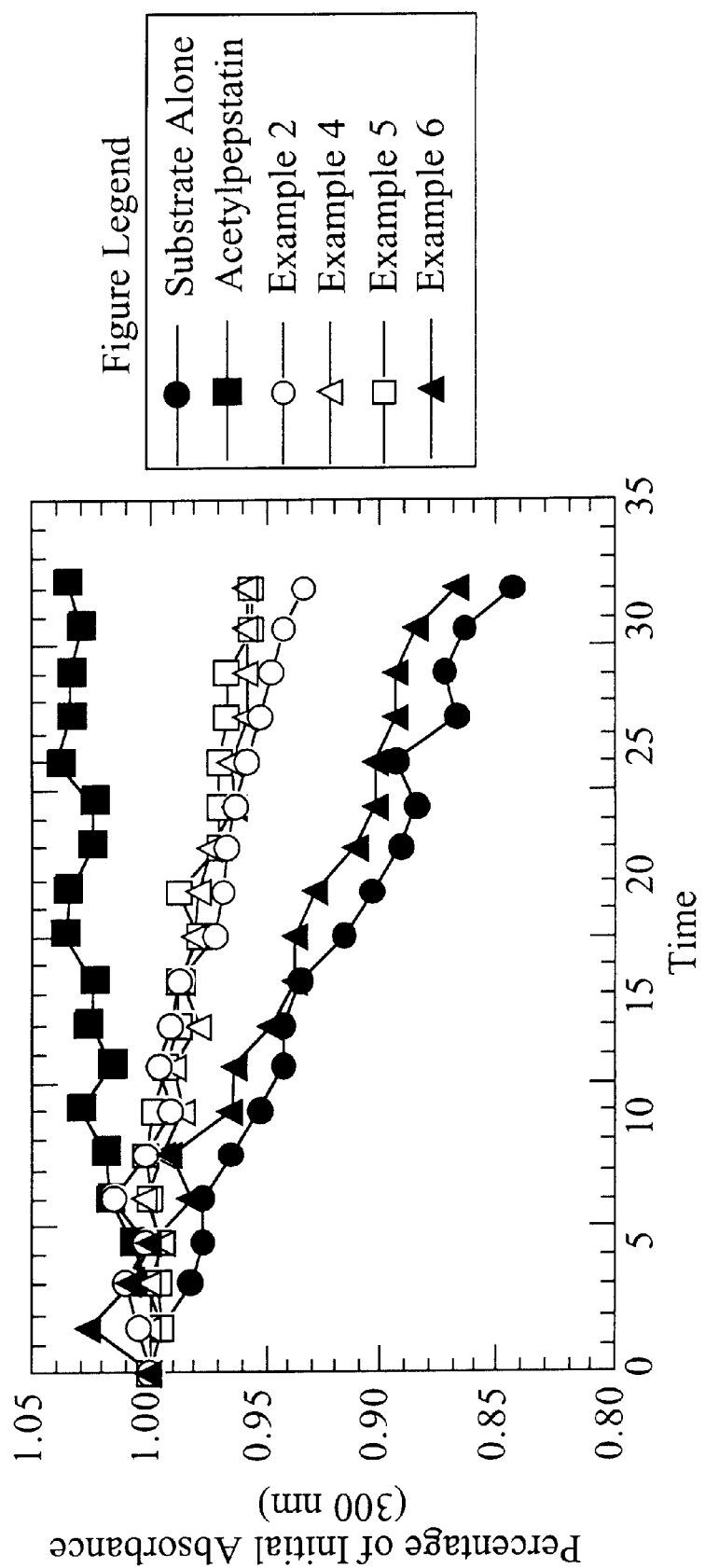
FIG. 3 is a graphical representation of the bioactivity of compounds prepared in Examples 1–5, without deprotection, at $1 \mu M$ in DMSO.

The next round of testing utilized the protected compounds from Examples 2, 4, 5, and 6 directly without prior deprotection of the tert-butyl esters. The compounds were again dissolved in DMSO. The results for the protected compounds tested at 1 μM are shown in FIG. 3 after normalization of the initial absorbance values. These compounds were tested in triplicate and the average values are shown in FIG. 3 along with the experimental standard deviations.

Preferred compounds and applications for practicing the invention have been described. It will be understood that the foregoing is illustrative only and that other compounds and applications can be employed without departing from the true scope of the invention defined in the following claims.

I Claim:

1. An aspartic protease/inhibitor complex comprising an aspartic protease and an aspartic protease inhibitor, said aspartic protease/inhibitor complex having said aspartic protease inhibitor chemically, physically and/or physico-chemically interacting with said aspartic protease and said aspartic protease inhibitor having the following general formula (I):

Z—Het—Z   (I)

wherein,
a) Het is a saturated, partially unsaturated or unsaturated and substituted or unsubstituted 3 to 7-membered heterocyclic ring having
 i) at least two heteroatoms, wherein the first heteroatom can interact with a first aspartate group in the active site of an aspartic protease and the second heteroatom can interact with a second aspartate group in the same active site, wherein at least one of the heteroatoms does interact with at least one of the first and second aspartate groups, and
 ii) a $pK_a$ value in the range from about 2.5 to about 12, and
b) wherein each Z can be the same or different, and has
 i) a shape complementarity with at least a portion of the substrate binding site of the aspartic protease;
 ii) a chemical structure for contacting multiple atoms of the substrate binding site; and
 iii) at least one R group, which can be the same or different, at least one R group having a chemical structure for occupying at least one sub-site, proximate to the active site of the aspartic protease.

2. The complex of claim 1, wherein the heteroatoms are selected from the group consisting of nitrogen, phosphorous, oxygen, sulfur, boron, silicon and combinations thereof.

3. The complex of claim 2, wherein at least one of the heteroatoms is nitrogen.

4. The complex of claim 1, wherein Z is a moiety having one or more atoms selected from the group consisting of hydrogen, carbon, nitrogen, oxygen, sulfur, boron, silicon, phosphorus, fluorine, chlorine, bromine, iodine and combinations thereof.

5. The complex of claim 1, wherein each heteroatom interacts with a carboxylic group of each aspartate group.

6. The complex of claim 1, wherein the contacting distance between non-hydrogen atoms of the Z groups and non-hydrogen atoms of the substrate binding site is ≦ about 4.1 Å.

7. The complex of claim 1, wherein there are at least about 50 contacts between atoms of the Z groups and atoms of the substrate binding site.

8. The complex of claim 1, wherein at least one Z has the structure having the general formula:

wherein Y is a moiety having a backbone chain of at least 2 atoms, and $R^1$ and $R^2$ are covalently bonded to the Y moiety, so that at least one of $R^1$ and $R^2$ is presented to the at least one sub-site.

9. The complex of claim 1, wherein at least one Z has the structure having the general formula:

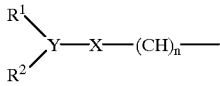

wherein Y is a moiety having a backbone chain of at least 2 atoms, $R^1$ and $R^2$ are covalently bonded to the Y moiety, so that at least one of $R^1$ and $R^2$ is presented to the at least one sub-site, X is a hydrogen bond-accepting group, and n=0, 1, 2 or 3.

10. The complex of claim 8, wherein each Y moiety is covalently bonded to each other through at least one hydrogen bond-accepting group, X, to form a cyclic structure having the general formula (III):

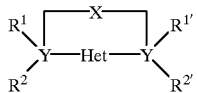

wherein $R^1$, $R^2$, $R^{1'}$, $R^{2'}$ can be the same or different and at least one of $R^1$, $R^{1'}$, $R^2$ and $R^{2'}$ has a chemical structure for occupying at least one sub-site, proximate to the active site of the aspartic protease.

11. The complex of claim 8, wherein atoms of the backbone chain are selected from the group consisting of carbon, nitrogen, phosphorus, sulfur, oxygen, silicon and combinations thereof.

12. The complex of claim 9, wherein atoms of the backbone chain are selected from the group consisting of carbon, nitrogen, phosphorus, sulfur, oxygen, silicon and combinations thereof.

13. The complex of claim 1, wherein the aspartic protease is HIV protease.

14. The complex of claim 1, wherein the aspartic protease is renin.

15. The complex of claim 1, wherein the aspartic protease is pepsin.

16. The complex of claim 1, wherein the aspartic protease is cathepsin D.

17. The complex of claim 1, wherein the heterocycle is selected from the group consisting of imidazole, imidazolidine, pyrazole, triazole, oxazole, thiazole, pyridazine, pyrimidine, pyrazine, piperazine, triazine, and oxazine.

18. An aspartic protease/inhibitor complex, comprising an aspartic protease and an aspartic protease inhibitor, said aspartic protease/inhibitor complex having said aspartic protease inhibitor chemically, physically and/or physicochemically interacting with said aspartic protease and said aspartic protease inhibitor having the following general formula (II):

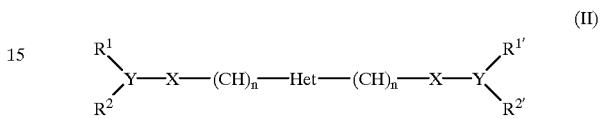

wherein,
a) Het is a saturated, partially unsaturated or unsaturated and substituted or unsubstituted 3 to 7-membered heterocyclic ring having
  i) at least two heteroatoms, wherein the first heteroatom can interact with a first aspartate group in the active site of an aspartic protease and the second heteroatom can interact with a second aspartate group in the same active site, wherein at least one of the heteroatoms does interact with at least one of the first and second aspartate groups, and
  ii) a $pK_a$ value in the range from about 2.5 to about 12, and
b) X is a hydrogen bond-accepting group;
c) Y is a moiety having a backbone chain of at least 2 atoms selected from the group consisting of carbon, nitrogen, phosphorus, sulfur, oxygen, silicon and combinations thereof;
d) each $R^1$, $R^{1'}$ $R^2$ and $R^{2'}$ group is covalently bonded to the Y moiety, and at least one of $R^1$, $R^{1'}$ $R^2$ and $R^{2'}$ has a chemical structure for occupying at least one of the $S_1$, $S_1'$, $S_2$ and $S_2'$ sub-sites; and
e) n=0, 1, 2 or 3.

19. The complex of claim 18, wherein the hydrogen bond-accepting group is selected from the group consisting of carbonyl, sulfoxide, sulfone, phosphine oxide, amine oxide and hydroxylamine groups.

20. The complex of claim 18, wherein Y is a moiety selected from the group consisting of substituted and unsubstituted, branched and unbranched alkyl, alkylamine, alkoxy, alkoxyamine, thioalkyl, thioalkoxy, thioalkoxyamine, thioalkylamine, phosphidoalkyl, phosphidoalkoxy, phosphidoalkoxyamine and phosphidoalkylamine groups.

21. The complex of claim 18, wherein $R^1$, $R^{1'}$ $R^2$ and $R^{2'}$ are the same or different and are selected from the group consisting of substituted and unsubstituted, branched and unbranched, $C_1$–$C_6$ alkanes, $C_1$–$C_6$ alkenes and $C_1$–$C_6$ alkynes; substituted and unsubstituted, branched and unbranched $C_3$–$C_9$ cycloalkanes and $C_3$–$C_9$ cycloalkenes; substituted and unsubstituted aromatic hydrocarbon and 3 to 10-membered heterocyclic rings; and amino acids.

22. The complex of claim 21, wherein one or more of $R^1$, $R^{1'}$ $R^2$ and $R^{2'}$ is substituted with one or more substituents selected from the group consisting of acyl, aldehyde, alkyl, amido, amino, aryl, carboxamide, carboxyl, ether, halo, hydroxyl, nitro, oxime, phosphido, sulfonyl and sulfoxide groups.

23. The complex of claim 22, wherein $R^1$ and $R^{1'}$ are the same or different and are selected from the group consisting of phenyl, benzyl, t-butyl, i-butyl, and i-propyl groups.

24. The complex of claim 23, wherein $R^2$ and $R^{2'}$ are the same or different and are selected from the group consisting of a tetrahydrofuranyl ring, a substituted benzamide, a 2-amino-1-hydroxyindan ring, and a substituted pyrazole.

25. An aspartic protease/inhibitor complex, comprising an aspartic protease and an aspartic protease inhibitor, said aspartic protease/inhibitor complex having said aspartic protease inhibitor chemically physically and/or physicochemically interacting with said aspartic protease and said aspartic protease inhibitor having the following general formula (III):

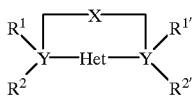

(III)

wherein,
  a) Het is a saturated, partially unsaturated or unsaturated and substituted or unsubstituted 3 to 7-membered heterocyclic ring having
    i) at least two heteroatoms, wherein the first heteroatom can interact with a first aspartate group in the active site of an aspartic protease and the second heteroatom can interact with a second aspartate group in the same active site, wherein at least one of the heteroatoms does interact with at least one of the first and second aspartate groups, and
    ii) a $pK_a$ value in the range from about 2.5 to about 12, and
  b) X is a hydrogen bond-accepting group;
  c) Y is a moiety having a backbone chain of at least 2 atoms selected from the group consisting of carbon, nitrogen, phosphorus, sulfur, oxygen, silicon and combinations thereof; and
  d) each $R^1$, $R^{1'}$, $R^2$ and $R^{2'}$ group is covalently bonded to the Y moiety, and at least one of $R^1$, $R^{1'}$, $R^2$ and $R^{2'}$ has a chemical structure for occupying at least one of the $S_1$, $S_1'$, $S_2$ and $S_2'$ sub-sites.

26. The complex of claim 25, wherein the hydrogen bond-accepting group is selected from the group consisting of carbonyl, sulfoxide, sulfone, phosphine oxide, amine oxide and hydroxylamine groups.

27. The complex of claim 25, wherein Y is a moiety selected from the group consisting of substituted and unsubstituted, branched and unbranched alkyl, alkylamine, alkoxy, alkoxyamine, thioalkyl, thioalkoxy, thioalkoxyamine, thioalkylamine, phosphidoalkyl, phosphidoalkoxy, phosphidoalkoxyamine and phosphidoalkylamine groups.

28. The complex of claim 25, wherein $R^1$, $R^{1'}$, $R^2$ and $R^{2'}$ are the same or different and are selected from the group consisting of substituted and unsubstituted, branched and unbranched, $C_1$–$C_6$ alkanes, $C_1$–$C_6$ alkenes and $C_1$–$C_6$ alkynes; substituted and unsubstituted, branched and unbranched $C_3$–$C_9$ cycloalkanes and $C_3$–$C_9$ cycloalkenes; substituted and unsubstituted aromatic hydrocarbon and 3 to 10-membered heterocyclic rings; and amino acids.

29. The complex of claim 28, wherein one or more of $R^1$, $R^{1'}$, $R^2$ or $R^{2'}$ is substituted with one or more substituents selected from the group consisting of acyl, aldehyde, alkyl, amido, amino, aryl, carboxamide, carboxyl, ether, halo, hydroxyl, nitro, oxime, phosphido, sulfonyl and sulfoxide groups.

30. The complex of claim 25; wherein $R^1$ and $R^{1'}$ are the same or different and selected from the group consisting of phenyl, benzyl, t-butyl, i-butyl, and i-propyl groups.

31. The complex of claim 25, wherein $R^2$ and $R^{2'}$ groups are the same or different and selected from the group consisting of a tetrahydrofuranyl ring, a substituted benzamide, a 2-amino-1-hydroxyindan ring, and a substituted pyrazole.

32. A method for inhibiting an aspartic protease comprising administering to a patient in need thereof a therapeutically effective amount of an aspartic protease inhibitor; said aspartic protease inhibitor having the following general formula (I):

$$Z\text{—Het—}$$ (I)

wherein,
  a) Het is a saturated, partially unsaturated or unsaturated and substituted or unsubstituted 3 to 7-membered heterocyclic ring having
    (i) at least two heteroatoms, wherein the first heteroatom can interact with a first aspartate group in the active site of an aspartic protease and the second heteroatom can interact with a second aspartate group in the same active site, wherein at least one of the heteroatoms does interact with at least one of the first and second aspartate groups, and
    (ii) a $pK_a$ value in the range from about 2.5 to about 12, and
  c) wherein each Z can be the same or different, and has
    (i) a shape complementarity with at least a portion of the substrate binding site of the aspartic protease;
    (ii) a chemical structure for contacting multiple atoms of the substrate binding site; and
    (iii) at least one R group, which can be the same or different, at least one R group having a chemical structure for occupying at least one sub-site, proximate to the active site of the aspartic protease.

33. The method of claim 32, wherein the heteroatoms are selected from the group consisting of nitrogen, phosphorous, oxygen, sulfur, boron, silicon and combinations thereof.

34. The method of claim 32, wherein at least one Z has the structure having the general formula:

wherein Y is a moiety having a backbone chain of at least 2 atoms, and $R^1$ and $R^2$ are covalently bonded to the Y moiety, so that at least one of $R^1$ and $R^2$ is presented to the at least one sub-site.

35. The method of claim 32, wherein at least one Z has the structure having the general formula:

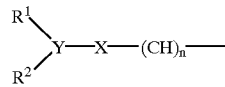

wherein Y is a moiety having a backbone chain of at least 2 atoms, $R^1$ and $R^2$ are covalently bonded to the Y moiety, so that at least one of $R^1$ and $R^2$ is presented to the at least one sub-site, X is a hydrogen bond-accepting group, and n=0, 1, 2 or 3.

36. The method of claim 32, wherein each Y moiety is covalently bonded to each other through at least one hydrogen bond-accepting group, X, to form a cyclic structure having the general formula (III):

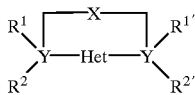

(III)

wherein $R^1$, $R^2$, $R^{1'}$, $R^{2'}$ can be the same or different and at least one of $R^1$, $R^{1'}$, $R^2$ and $R^{2'}$ has a chemical structure for occupying at least one sub-site, proximate to the active site of the aspartic protease.

37. The method of claim 34, wherein the heterocycle is selected from the group consisting of imidazole, imidazolidine, pyrazole, triazole, oxazole, thiazole, pyridazine, pyrimidine, pyrazine, piperazine, triazine, and oxazine.

38. A compound selected from the group consisting of:
4,5-bis{[(1,1-dimethylethoxy)-(S)-phenylalanyl]carbonyl}-1H-imidazole,
4,5-bis{[(1,1-dimethylethoxy)-(S)-phenylalanyl]carbonyl}-1H-pyrazole,
4,5-bis{[(1,1-dimethylethoxy)-(S)-phenylalanyl]carbonyl}-1H-triazole,
4,5-bis{[(1,1-dimethylethoxy)-(S)-phenylalanyl]carbonyl}-1H-imidazoline,
4,5-bis{[(1,1-dimethylethoxy)-(S)-phenylalanyl]carbonyl}-1H-oxazole,
4,5-bis{[(1,1-dimethylethoxy)-(S)-phenylalanyl]carbonyl}-1H-thiazole,
4,5-bis{[(1,1-dimethylethoxy)-(S)-phenylalanyl]carbonyl}-1H-pyridazine,
4,5-bis{[(1,1-dimethylethoxy)-(S)-phenylalanyl]carbonyl}-1H-pyrimidine,
4,5-bis{[(1,1-dimethylethoxy)-(S)-phenylalanyl]carbonyl}-1H-pyrazine,
4,5-bis{[(1,1-dimethylethoxy)-(S)-phenylalanyl]carbonyl}-1H-piperazine,
4,5-bis{[(1,1-dimethylethoxy)-(S)-phenylalanyl]carbonyl}-1H-triazine,
4,5-bis{[(1,1-dimethylethoxy)-(S)-phenylalanyl]carbonyl}-1H-oxazine,
3,5-bis{[(1,1-dimethylethoxy)-(S)-phenylalanyl]carbonyl}-1H-imidazole,
3,5-bis{[(1,1-dimethylethoxy)-(S)-phenylalanyl]carbonyl}-1H-pyrazole,
3,5-bis{[(1,1-dimethylethoxy)-(S)-phenylalanyl]carbonyl}-1H-triazole,
3,5-bis{[(1,1-dimethylethoxy)-(S)-phenylalanyl]carbonyl}-1H-imidazoline,
3,5-bis{[(1,1-dimethylethoxy)-(S)-phenylalanyl]carbonyl}-1H-oxazole,
3,5-bis{[(1,1-dimethylethoxy)-(S)-phenylalanyl]carbonyl}-1H-thiazole,
3,5-bis{[(1,1-dimethylethoxy)-(S)-phenylalanyl]carbonyl}-1H-pyridazine,
3,5-bis{[(1,1-dimethylethoxy)-(S)-phenylalanyl]carbonyl}-1H-pyrimidine,
3,5-bis{[(1,1-dimethylethoxy)-(S)-phenylalanyl]carbonyl}-1H-pyrazine,
3,5-bis{[(1,1-dimethylethoxy)-(S)-phenylalanyl]carbonyl}-1H-piperazine,
3,5-bis{[(1,1-dimethylethoxy)-(S)-phenylalanyl]carbonyl}-1H-triazine,
3,5-bis{[(1,1-dimethylethoxy)-(S)-phenylalanyl]carbonyl}-1H-oxazole,
4,5-bis{{[(1,1-dimethylethoxy)-(S)-valyl]-(S)-phenylalanyl}carbonyl}-1H-imidazole,
4,5-bis{{[(1,1-dimethylethoxy)-(S)-valyl]-(S)-phenylalanyl}carbonyl}-1 H-pyrazole, 4,5-bis{{[(1,1-dimethylethoxy)-(S)-valyl]-(S)-phenylalanyl}carbonyl}-1H-triazole, 4,5-bis{{[(1,1-dimethylethoxy)-(S)-valyl]-(S)-phenylalanyl}carbonyl}-1H-imidazoline, 4,5-bis{{[(1,1-dimethylethoxy)-(S)-valyl]-(S)-phenylalanyl}carbonyl}-1H-oxazole, 4,5-bis{{[(1,1-dimethylethoxy>(S)-valyl]-(S)phenylalanyl}carbonyl}1H-thiazole, 4,5-bis{{[(l1,1-dimethylethoxy)-(S)-valyl]-(S)-phenylalanyl}carbonyl}-1H-pyridazine, 4,5-bis{{[(1,1-dimethylethoxy)-(S)-valyl]-(S)-phenylalanyl}carbonyl}-1H-pyrimidine, 4,5-bis{{[(1,1-dimethylethoxy)-(S)-valyl]-(S)-phenylalanyl}carbonyl}-1 H-pyrazine, 4,5-bis{{([(1,1-dimethylethoxy)-(S)-valyl]-(S)-phenylalanyl}carbonyl}-1H-piperazine, 4,5-bis{{[(1,1-dimethylethoxy)-(S)-valyl]-(S)-phenylalanyl}carbonyl}-1H-triazine, 4,5-bis{{[(1,1-dimethylethoxy)-(S)-valyl]-(S)-phenylalanyl}carbonyl}-1H-oxazine, 3,5-bis{{[(1,1-dimethylethoxy)-(S)-valyl]-(S)-phenylalanyl}carbonyl}-1H-imidazole, 3,5-bis{{[(1,1-dimethylethoxy)-(S)-valyl]-(S)-phenylalanyl}carbonyl 1H-pyrazole, 3,5-bis{{[(1,1-dimethylethoxy)-(S)-valyl]-(S)-phenylalanyl}carbonyl}-1H-triazole, 3,5-bis{{[(1,1-dimethylethoxy)-(S)-valyl]-(S)-phenylalanyl}carbonyl}-1H-imidazoline, 3,5-bis{{[(1,1-dimethylethoxy)-(S)-valyl]-(S)-phenylalanyl}carbonyl}-1H-oxazole, 3,5-bis{{[(1,1-dimethylethoxy)-(S)-valyl]-(S)-phenylalanyl}carbonyl}-1H-thiazole, 3,5-bis{{[(1,1-dimethylethoxy)-(S)-valyl]-(S)-phenylalanyl}carbonyl}-1H-pyridazine, 3,5-bis{{[(1,1 -dimethylethoxy)-(S)-valyl]-(S)-phenylalanyl}carbonyl}-1H-pyrimidine, 3,5-bis{{[(1,1-dimethylethoxy(S)-valyl]-(S)-phenylalanyl}carbonyl}-1H-pyrazine, 3,5-bis{{[(1,1-dimethylethoxy)-(S)valyl]-(S)-phenylalanyl}carbonyl}-1H-piperazine, 3,5-bis{[(1,1-dimethylethoxy)-(S)-valyl]-(S)-phenylalanyl}carbonyl}-1H-triazine, and 3,5-bis{{[(1,1-dimethylethoxy)-(S)-valyl]-(S)-phenylalanyl}carbonyl}-1H-oxazine.

* * * * *

UNITED STATES PATENT AND TRADEMARK OFFICE
CERTIFICATE OF CORRECTION

PATENT NO. : 6,184,241 B1
DATED : February 6, 2001
INVENTOR(S) : Paul W. Baures

It is certified that error appears in the above-identified patent and that said Letters Patent is hereby corrected as shown below:

Column 20,
Line 14, the formula, "Z-Het-" should read -- "Z-Het-Z";

Column 21,
Line 13, the claim reference "34" should read -- 32 --;

Column 22,
Line 20, should read -- "[(1,1-dimethylethoxy)-(S)-valyl]-(S)-" --;
Line 21, should read -- "phenylalanyl}carbonyl}-1H-thiazole, 4,5-bis{{[(1,1";
Line 27, should read "bis{{[(1,1-dimethylethoxy)-(S)-valyl]-(S)-";
Line 34, should read -- "valyl]-(S)-phenylalanyl}carbonyl}-1H-pyrazole, 3,5-bis{{";
Line 45, should read -- "bis{{[(1,1-dimethylethoxy)-(S)-valyl]-(S)-"; and
Line 49, should read --"1H-piperazine, 3,5-bis {{[(1,1-dimethylethoxy)-(S)-valyl]-".

Signed and Sealed this

Twentieth Day of November, 2001

*Attest:*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO. : 6,184,241 B1
DATED : February 6, 2001
INVENTOR(S) : Paul W. Baures

Page 1 of 1

It is certified that error appears in the above-identified patent and that said Letters Patent is hereby corrected as shown below:

Column 20,
Line 14, the formula, "Z-Het-" should read -- "Z-Het-Z";

Column 21,
Line 13, the claim reference "34" should read -- 32 --;

Column 22,
Line 20, should read -- "[(1,1-dimethylethoxy)-(S)-valyl]-(S)-" --;
Line 21, should read -- "phenylalanyl}carbonyl}-1H-thiazole, 4,5-bis{{[(1,1";
Line 27, should read "bis{{[(1,1-dimethylethoxy)-(S)-valyl]-(S)-";
Line 34, should read -- "valyl]-(S)-phenylalanyl}carbonyl}-1H-pyrazole, 3,5-bis{{";
Line 45, should read -- "bis{{[(1,1-dimethylethoxy)-(S)-valyl]-(S)-"; and
Line 49, should read --"1H-piperazine, 3,5-bis {{[(1,1-dimethylethoxy)-(S)-valyl]-".

Signed and Sealed this

Twenty-seventh Day of November, 2001

Attest:

NICHOLAS P. GODICI
Attesting Officer
Acting Director of the United States Patent and Trademark Office